US006743965B2

(12) United States Patent
Yang et al.

(10) Patent No.: US 6,743,965 B2
(45) Date of Patent: *Jun. 1, 2004

(54) APERTURED POLYMERIC FILM WEB WITH DIOL/SURFACTANT ADDITIVE

(75) Inventors: Ching-Yun Morris Yang, Princeton Junction, NJ (US); Dietmar Van Loyen, Wuppertal (DE); Anthony DiSalvo, Bernardsville, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/745,898

(22) Filed: Dec. 21, 2000

(65) Prior Publication Data

US 2002/0123731 A1 Sep. 5, 2002

(51) Int. Cl.$^7$ ................................................. A61F 13/15
(52) U.S. Cl. .................. 604/367; 604/385.18; 604/383; 604/904; 442/118; 428/131
(58) Field of Search ................................ 604/370, 383, 604/385.17, 385.18; 428/131, 132, 137, 138; 442/118

(56) References Cited

U.S. PATENT DOCUMENTS

| 3,343,225 A | 9/1967 | Hochstrasser et al. |
| 3,348,866 A | 10/1967 | Etz |

(List continued on next page.)

FOREIGN PATENT DOCUMENTS

| DE | 4311882 | 4/1994 |
| EP | 0422660 B1 | 2/1994 |
| EP | 0623333 A2 A3 | 11/1994 |
| EP | 0639363 B1 | 2/1995 |
| WO | WO 94/28846 A | 12/1994 |
| WO | WO 94/28848 | 12/1994 |
| WO | WO 95/23571 | 9/1995 |
| WO | WO 97/09013 | 3/1997 |
| WO | WO 97/09017 A | 3/1997 |
| WO | WO 97/09017 | 3/1997 |
| WO | WO 98/10726 | 3/1998 |
| WO | WO 99/25288 | 5/1999 |
| WO | WO 00/25715 A | 5/2000 |
| WO | WO 00/27515 | 8/2000 |
| WO | WO 00/64501 A | 11/2000 |
| WO | WO 00/64501 | 11/2000 |
| WO | WO 01/01905 | 1/2001 |
| WO | WO 01/01905 A | 1/2001 |
| WO | WO 01/01908 | 1/2001 |
| WO | WO 01/01909 A | 1/2001 |

OTHER PUBLICATIONS

PCT International Search Report PCT/US01/49008 dated Aug. 23, 2002.
U.S. patent application Ser. No. 09/343,759 (PPC–668).
U.S. patent application Ser. No. 09/345,090 (PPC–691).
U.S. patent application Ser. No. 09/345,089 (PPC–713).
U.S. patent application Ser. No. 09/742,611 (PPC–769).
U.S. patent application Ser. No. 09/343,760 (J&J 1810).
U.S. patent application Ser. No. 09/606,559 (J&J 1924).
U.S. patent application Ser. No. 09/607,032 (J&J 1925).

*Primary Examiner*—Weilun Lo
*Assistant Examiner*—Jamisue A. Webb

(57) ABSTRACT

An apertured film cover for an absorbent article is disclosed. The cover has an additive combination comprising a diol and a surfactant applied thereto. The additive combination provides surprisingly improved fluid transfer across the cover. It can also provide a benefit by reducing frictional forces during the manufacture of a tampon.

38 Claims, 1 Drawing Sheet

U.S. PATENT DOCUMENTS

| | | |
|---|---|---|
| 3,422,496 A | 1/1969 | Wolff et al. |
| 3,477,102 A | 11/1969 | Etz |
| 3,515,138 A | 6/1970 | Hochstrasser et al. |
| 3,683,912 A | 8/1972 | Olson et al. |
| 3,688,346 A | 9/1972 | Johst et al. |
| 3,724,465 A | 4/1973 | Duchane |
| 3,796,219 A | 3/1974 | Hanke |
| 3,852,847 A | 12/1974 | Etz |
| 4,081,884 A | 4/1978 | Johst et al. |
| 4,109,354 A | 8/1978 | Ronc |
| 4,453,296 A | 6/1984 | Friese |
| 4,498,218 A | 2/1985 | Friese |
| 4,582,717 A | 4/1986 | Von Bltterset al. |
| 4,816,100 A | 3/1989 | Friese |
| 4,836,450 A | 6/1989 | Hunter |
| 4,859,273 A | 8/1989 | Friese |
| 5,135,472 A | 8/1992 | Hermann et al. |
| 5,342,334 A | 8/1994 | Thompson et al. |
| 5,592,725 A | 1/1997 | Brinker |
| 5,647,862 A | 7/1997 | Osborn, III et al. |

APERTURED POLYMERIC FILM WEB WITH DIOL/SURFACTANT ADDITIVE

CROSS REFERENCE TO RELATED APPLICATIONS

This invention is related to the following copending applications: U.S. Ser. No. 09/343,759, filed Jun. 30, 1999, entitled "Continuous Method of Providing Individual Sheets from a Continuous Web"; U.S. Ser. No. 09/345,090, filed Jun. 30, 1999, entitled "Multilayered Apertured Film Wrapping Element for Absorbent Articles"; U.S. Ser. No. 09/345,089, filed Jun. 30, 1999, entitled "Heterogeneous Apertured Film Wrapping Element for Absorbent Articles"; U.S. Ser. No. 09/343,760, filed Jun. 30, 1999, entitled "Domed Tampon with Surfactant-Treated Cover"; U.S. Ser. No. 09/606,958, filed Jun. 29, 2000, entitled "Sealing Roller and Sealing Roller Element, Particularly for Producing a Tampon for Feminine Hygiene and Method Therefore"; U.S. Ser. No. 09/607,032, filed Jun. 29, 2000, entitled "Tampon Having Apertured Film Cover Thermobonded to Fibrous Absorbent Structure"; U.S. Ser. No. 09/606,559, filed Jun. 29, 2000, entitled "Tampon for Feminine Hygiene and Process and Apparatus for its Production"; and U.S. Ser. No. 09/742,611, filed on Dec. 21, 2000, entitled "Apertured Polymeric Film Web with Surfactant Mixture Additive".

FIELD OF THE INVENTION

The present invention relates to an apertured film material useful as a body-side liner of an absorbent article. The film material has an additive combination applied to its surface. The additive combination provides improved fluid transfer across the cover, and it is capable of reducing frictional forces during processing of the absorbent article.

BACKGROUND OF THE INVENTION

There are several types of covers that have been or are currently in use for tampons: woven fabrics, nonwoven fabrics, apertured films, reticulated films, polymer nets, and the like. While the patent literature has suggested that a progression from nonwoven fabrics to apertured films in these covers is desired, this has not yet occurred commercially. In order to commercialize this desirable tampon, several issues must be overcome. First, apertured films are generally hydrophobic in nature, and this can reduce the ease with which bodily fluids can be accepted into the absorbent structure enclosed within the covers. Second, apertured films have significantly different friction characteristics than nonwoven fabrics. This can create processing difficulties, especially in tampon presses in which compressed tampons are subjected to axial ejection forces, such as disclosed in U.S. Pat. No. 3,343,225 (Hochstrasser et al.), U.S. Pat. No. 3,348,866 (Etz), U.S. Pat. No. 3,422,496 (Wolff et al.), U.S. Pat. No. 3,477,102 (Etz) U.S. Pat. No. 3,515,138 (Hochstrasser et al.), U.S. Pat. No. 3,688,346 (Johst et al.), U.S. Pat. No. 3,852,847 (Etz ), U.S. Pat. No. 4,081,884 (Johst et al.), U.S. Pat. No. 4,498,218 (Friese), and U.S. Pat. No. 4,453,296 (Friese), European Pat. App. No. 0 623 333 (Karl Ruggli AG), European Pat. App. No. 0 639 363 (Karl Ruggli AG), and European Pat. No. 0 422 660 (Johnson & Johnson GmbH).

Nonwoven fabric covers may be incorporated into tampons as described in Friese, U.S. Pat. Nos. 4,816,100; 4,836,450; and 4,859,273. These tampons can then be made into tampons as described in the patents identified above.

Apertured film covers have been incorporated into sanitary napkins to increase the products' ability to hide absorbed bodily fluids. An example of such an apertured film cover is disclosed in McNeil-PPC, Inc., EP 0 900 071. This advancement relates to the corona treatment of an apertured film for application thereon of a water-borne surfactant. This significant advance in the art, nonetheless requires numerous processing steps, and there sanitary napkins produced therefrom are not subjected to the high axial friction seen in the tampon manufacturing processes described above.

Therefore, what is needed is an apertured film material useful as a body-side liner or cover of an absorbent article, such as a tampon, that is processable in a commercially efficient manner, that provides satisfactory fluid transport into the absorbent article, and that aids in removal of the tampon from an overwrapper or applicator prior to and/or during use.

SUMMARY OF THE INVENTION

The present invention relates to a polymeric film material useful as a body-side liner of an absorbent article. The film material comprises an apertured polymeric film web and an additive combination applied thereto. The additive combination is formed of about 10 to about 90 wt-% of a diol and about 90 to about 10 wt-% of a surfactant. The film material exhibits a sinking basket test time of less than about 25 seconds.

The present invention also relates to a catamenial tampon comprising an absorbent structure, a withdrawal string, and the polymeric film material described above substantially enclosing the absorbent structure.

The invention further relates to a process for the manufacture of a tampon. The process includes a) applying up to about 1 gsm of an additive composition to a web of fluid-impervious plastic material formed into an apertured film material b) separating an individual sheet from the web;

c) attaching the individual sheet to an absorbent sliver;

d) forming the absorbent sliver into a tampon blank;

e) compressing the tampon blank in a press; and f) applying an ejection force to the compressed tampon in an axial direction to eject the tampon from the press.

In the above process, the additive combination comprises about 10 to about 90 wt-% of a diol and about 90 to about 10 wt-% of a surfactant, and the film material provides a sinking basket test time of less than about 25 seconds. Further, when the tampon blank is formed, the individual sheet substantially encloses it. The compressed tampon is substantially cylindrical, and it has an outer cover comprising the individual sheet.

DETAILED DESCRIPTION OF THE PREFERRED EMBODIMENT

Figure 1:
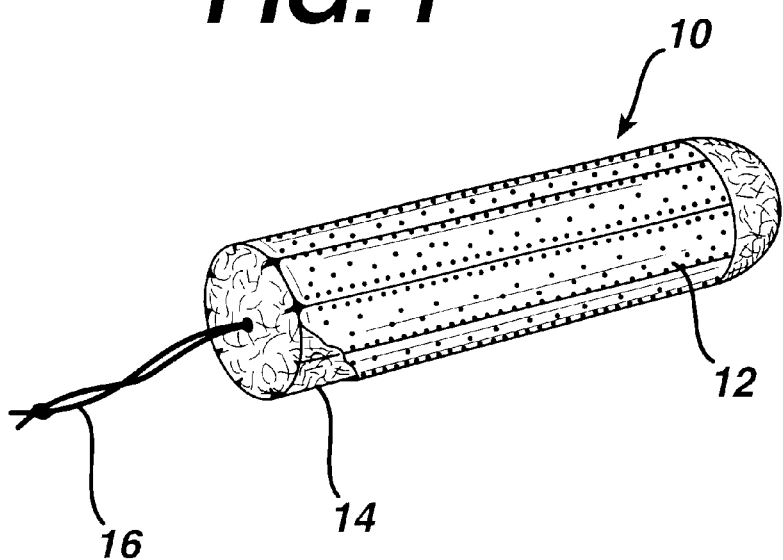
FIG. 1 is a perspective view of a tampon having an apertured film cover according to the present invention.

The present invention relates to polymeric film material useful as a body-side liner of an absorbent article, and it is described below in this context.

As used herein, the term "absorbent article" generally refers to devices used to absorb and contain body exudates, and more specifically, to devices that are placed against, in proximity to, or inside the body of the wearer to absorb and contain such body exudates. The term includes, without limitation, diapers, catamenial pads, tampons, sanitary napkins, incontinent pads, training pants, and the like, as well as wipes, bandages, and wound dressings.

As used herein, the term "apertured film" refers to a fluid-impervious plastic material in the form of a resilient three-dimensional web having first and second surfaces. The first surface of the three-dimensional web has a multiplicity of apertures therein. Preferably, each of the apertures is defined by a multiplicity of intersecting elements interconnected to one another substantially in the plane of the first surface. Each of the elements exhibits a cross-section, preferably having a base portion in the plane of the first surface and a sidewall joined to each edge of the base portion. The sidewall portions extend generally in the direction of the second surface of the three-dimensional web. Further, the intersecting sidewall portions are interconnected to one another intermediate the first and second surfaces of the web. The interconnected sidewall portions preferably terminate substantially concurrently with one another in the plane of the second surface.

The absorbent article 10 of the present invention comprises an apertured film body-side liner or cover 12, and an absorbent structure 14. It may also include a liquid-impervious liner, such as a backsheet of a sanitary napkin. The cover 12 at least partially encloses the absorbent structure 14 that is generally designed and constructed to absorb and contain bodily exudates. The absorbent article 10 also includes placement elements, such as an adhesive, and/or removal elements, such as a withdrawal string 16. While the absorbent article 10 may be any product as defined above, the following relates to a particularly preferred embodiment, a catamenial tampon.

The absorbent structure may be any absorbent means that is capable of absorbing and/or retaining liquids (e.g., menses and/or urine). The absorbent structure can be manufactured in a wide variety of sizes and shapes and from a wide variety of liquid-absorbing materials. A representative, non-limiting list of useful materials includes cellulosic materials, such as rayon, cotton, wood pulp, creped cellulose wadding, tissue wraps and laminates, peat moss, and chemically stiffened, modified, or cross-linked cellulosic fibers; synthetic materials, such as polyester fibers, polyolefin fibers, absorbent foams, absorbent sponges, superabsorbent polymers, absorbent gelling materials; formed fibers, such as capillary channel fibers and multilimbed fibers; combinations of materials, such as synthetic fibers and wood pulp including coformed fibrous structures (e.g., those materials described in Anderson et al., U.S. Pat. No. 4,100,324); or any equivalent material or combinations of materials, or mixtures of these.

The placement elements may be any element or device that is useful to secure the absorbent article 10 during use. A representative, non-limiting list of useful placement elements includes adhesives, tape tabs, wings, hook-and-loop fasteners, and the like. Preferable placement elements include adhesives.

The removal elements may be any element or device that is useful to remove the tampon from the bodily cavity after use. A representative, non-limiting list of useful removal elements includes string, including spun fibers and monofilament line, tape, and the like. Preferable removal elements include string.

The polymeric film material of the present invention is formed of a web having first surface and second surface having an additive combination applied thereto. The web may be formed of a homogeneous monolayer film; a heterogeneous, monolayer film, such as is described in the commonly assigned, corresponding application U.S. Ser. No. 09/345,089, filed Jun. 30, 1999, entitled "Heterogeneous Apertured Film Wrapping Element for Absorbent Articles", the disclosure of which is hereby incorporated by reference; or it may be formed of a laminate having a plurality of layers, such as is described in the commonly assigned, corresponding application U.S. Ser. No. 09/345,090, filed Jun. 30, 1999, entitled "Multilayered Apertured Film Wrapping Element for Absorbent Articles", the disclosure of which is hereby incorporated by reference.

The polymeric film material may be formed of a single thermoplastic polymeric material, and it may also be formed of at least one blend of at least two immiscible polymeric materials. A representative, non-limiting list of polymeric materials that may be used in the apertured film includes polyolefins, such as polypropylene and polyethylene; polyolefin copolymers, such as ethylene-vinyl acetate ("EVA"), ethylene-propylene, ethylene-acrylates, and ethylene-acrylic acid and salts thereof; halogenated polymers; polyesters and polyester copolymers; polyamides and polyamide copolymers; polyurethanes and polyurethane copolymers; polystyrenes and polystyrene copolymers; and the like. Preferred polymeric materials include polyolefins, especially polyethylene and polypropylene and ethylene copolymers, especially EVA.

In a heterogeneous apertured film, either monolayer or multilayer, the film preferably includes a blend of at least two thermoplastic polymeric components. The first thermoplastic polymeric component forms a continuous phase that exhibits a first melting point temperature. In order to form the continuous phase, it is preferred that the first thermoplastic polymeric component be present at about 45 to about 95 wt-% of the layer, more preferably about 60 to about 80 wt-% of the layer. A dispersed phase comprises a second thermoplastic polymeric component that exhibits a second melting point temperature. It is preferred that the second thermoplastic polymeric component is present at about 55 to about 5 wt-% of the layer, more preferably about 80 to about 60 wt-% of the layer. In addition, the second melting point temperature is sufficiently less than the first melting point temperature to allow the film to be heated to a temperature between the first and second melting point temperatures, rendering the second thermoplastic polymeric component capable of forming an adhesive bond. This bond may be formed between different portions of the cover, or it may be between the cover and another element of the tampon.

In addition, other components and further additives can be added to the polymeric material in an amount that will not hinder obtaining the object of the present invention, including, without limitation, antioxidants, UV absorbers, lubricants, antiblock and slip agents, plasticizers, nucleating agents, antistatic agents, flame retardants, pigments, dyes, and inorganic or organic fillers.

The additive combination applied to the cover may serve at least two functions. First, it renders hydrophilic an apertured film that comprises generally hydrophobic polymeric materials. This is especially helpful to reduce by-pass leakage of body exudates around the absorbent article. Second, it can significantly reduce manufacturing process friction, such as ejection forces when the tampon is ejected from a tampon forming press in an axial direction. Therefore, the additive combination has properties that improve the affinity of the apertured film for bodily fluids and reduces friction between the tampon (or other absorbent article) and manufacturing equipment. The additive combination comprises about 10 to about 90 wt-% of the diol and about 90 to about 10 wt-% of the surfactant. More preferably, the additive combination comprises about 25 to about 75 wt-% of the diol and about 75 to about 25 wt-% of the surfactant, and most preferably, the additive combination comprises about 40 to about 60 wt-% of the diol and about 60 to about 40 wt-% of the surfactant.

A representative, non-limiting list of useful diols includes $C_{2-8}$ diols and polyglycols, and the like. Preferably, the diol is selected from the group consisting of glycols ($C_2$ and $C_3$ diols) and polyglycols. As used in the specification and the claims, the term "polyglycol" refers to a dihydroxy ether formed by dehydration of two or more glycol molecules. A representative, non-limiting list of useful polyglycols includes ethylene glycol, propylene glycol, polyethylene glycols, plypropylene glycols, methoxypolyethylene glycols, polybutylene glycols, or block copolymers of butylene oxide and ethylene oxide. Among the aforementioned polyglycols, polyethylene glycol having a molecular weight of less than about 600, and polypropylene glycol having a molecular weight of less than about 4,000, are preferred. A polyglycol that is liquid at room temperature is most preferred.

As used herein, the term "surfactant" refers to a surface active agent, i.e., one that modifies the nature of surfaces. Surfactants are often used as wetting agents, detergents, emulsifiers, dispersing agents, penetrants, and antifoaming agents. Surfactants may be anionic, cationic, nonionic and ampholytic. Preferably, the surfactant used in the present invention is a nonionic surfactant. Nonionic surfactants are generally less irritating of human body tissue, and they are therefore more acceptable in uses that contact such tissue.

As used herein, the term "hydrophilic agent" refers to a substance that readily associates with water, and the term "lyophilic agent" refers to an agent that attracts liquids in a colloid system, describing a colloidal system in which the dispersed phase is a liquid and attracts the dispersing medium. One measure of the relative hydrophilicity and lyophilicity of an agent is the HLB or hydrophile-lyophile balance with a high HLB reflecting a relatively hydrophilic agent and a low HLB reflecting a relatively lyophilic agent. Preferably the hydrophilic agent has an HLB of at least about 10, more preferably, it has an HLB of at least about 12, and most preferably, it has an HLB of at least about 15. However, hydrophilic agents that do not typically have a measured HLB can also be used. Such hydrophilic agents can include, without limitation, diols, such as glycols and polyglycols. Conversely, preferred lyophilic agents have an HLB of less than about 10, more preferably, less than about 8, and most preferably, less than about 5.

A representative, non-limiting list of useful diols includes $C_{2-8}$ diols and polyglycols, and the like. Preferably, the diol is selected from the group consisting of glycols ($C_2$ and $C_3$ diols) and polyglycols. As used in the specification and the claims, the term "polyglycol" refers to a dihydroxy ether formed by dehydration of two or more glycol molecules. A representative, non-limiting list of useful polyglycols includes ethylene glycol, propylene glycol, polyethylene glycols, plypropylene glycols, methoxypolyethylene glycols, polybutylene glycols, or block copolymers of butylene oxide and ethylene oxide. Among the aforementioned polyglycols, polyethylene glycol having a molecular weight of less than about 600, and polypropylene glycol having a molecular weight of less than about 4,000, are preferred. A polyglycol that is liquid at room temperature is most preferred.

Preferred nonionic surfactants are ethoxylates, including fatty acid ester ethoxylates, fatty acid ether ethoxylates, and ethoxylated sugar derivatives.

One particularly preferred class of ethoxylated fatty acid esters is the class of ethoxylated fatty acid polyolesters, and more particularly, ethoxylated fatty acid sorbitan ester. A representative, non-limiting list of useful ethoxylated fatty acid sorbitan esters includes polyoxyethylene sorbitan laurate (also known as Polysorbate 20 (HLB: 16.7) and 21 (HLB: 13.3)), polyoxyethylene sorbitan palmitate (also known as Polysorbate 40 (HLB: 15.6)), polyoxyethylene sorbitan stearate (also known as Polysorbate 60 (HLB: 14.9) and 61 (HLB: 9.6)), polyoxyethylene sorbitan tristearate (also known as Polysorbate 65 (HLB: 10.5)), polyoxyethylene sorbitan oleate (also known as Polysorbate 80 (HLB: 15.0) and 81 (HLB: 10.0)), and polyoxyethylene sorbitan trioleate (also known as Polysorbate 85 (HLB:11.0)). Among the aforementioned ethoxylated fatty acid sorbitan esters, polyoxyethylene-20-sorbitan monolaurate is most preferred.

One particularly preferred class of ethoxylated fatty acid ethers is the class of polyoxyethylene alkyl ether. A representative, non-limiting list of useful polyoxyethylene alkyl ethers includes polyoxyethylene lauryl ether, polyoxyethylene stearyl ether (also known as Steareth-2, Steareth-10 (HLB: 12.4), and the like), polyoxyethylene cetyl ether (also known as Ceteth-2, Ceteth-10 (HLB: 12.9), and the like), and polyoxyethylene oleyl ether (also known as Oleth-2 (HLB: 12.4), Oleth-10, and the like). Among the aforementioned polyoxyethylene alkyl ethers, polyoxyethylene stearyl ether is most preferred.

One particularly preferred class of fatty acid esters is the class of sorbitan fatty acid esters. A representative, non-limiting list of useful sorbitan fatty acid esters includes sorbitan monooleate (HLB: 4.3), sorbitan monostearate (HLB: 4.7), sorbitan monopalmitate (HLB: 6.7), sorbitan monolaurate (HLB: 8.6), sorbitan tristearate (HLB: 2.1), and sorbitan trioleate (HLB: 1.8). Among the aforementioned sorbitan fatty acid esters, sorbitan monooleate is most preferred.

One particularly preferred class of ethoxylated sugar derivatives is the class of methyl glucose derivatives. A representative, non-limiting list of useful methyl glucose derivatives includes methyl gluceth-10, methyl glucose-20, methyl glucose-20 distearate, methyl glucose dioleate (HLB: 5), and methyl glucose sesquistearate (HLB: 6), PEG-120 methyl glucose dioleate, and PEG-20 methyl glucose sesquistearate.

It is to be understood that the components of the additive combinations used in the tampon and in its manufacture as described herein are commercially available. Examples thereof are marketed under the registered trademarks "SPAN" (sorbitan derivatives), "TWEEN" (polysorbate derivatives), and "BRIJ" (polyoxyethylene oleyl ethers) of UNIQEMA, a division of ICI, Wilmington, Del., USA and under the registered trademarks "GLUCAM" (methyl glucose ethers), "GLUCATE" (methyl glucose derivatives), and "GLUCAMATE" (polyethyleneglycol ethers of methyl glucoses) of Amerchol Corporation, Edison, N.J., USA.

The additive combination is, preferably, applied to the cover in an amount of up to about 1 g/m² ("gsm"). More preferably, the coating weight is about 0.05 to about 0.8 gsm, and most preferably, it is applied at a coating weight of about 0.2 to about 0.5 gsm. If too little additive combination is applied, the product will not have adequate fluid transfer across the polymeric film material, and the cover may also be damaged in the manufacturing process, especially during its axial ejection from the tampon press. Too much additive combination is uneconomical, and it may be detectable by the consumer. In addition, if too much is applied, the excess tends to build up on the manufacturing equipment, and extraneous material (such as dirt, fibers, and the like) can become adhered to the machine. This can also result in poor control of the cover material, misplacement of the cover, and loose ends of the cover after cover attachment.

The add-on amount of the additive combination described above should be sufficient to reduce process friction, such as tampon press ejection forces, sufficiently to prevent damage to the product during manufacture. Damage to the product includes destroying the product due to press jams in which the product stops the machine. Damage to the product also includes distortion of the cover due to friction between the cover and manufacturing equipment. This may be viewed as "shingling" of the product. Shingling of the product occurs when pleats perpendicular to the tampon's longitudinal axis are formed. This may take the appearance of a series of rings around the products due to these circumferential pleats. Preferably, the nonionic surfactant is applied to the cover in an amount sufficient to reduce tampon press ejection forces to less than about 1100 N. More preferably, the tampon press ejection forces are reduced to less than about 1000 N.

Again, the absorbent structure can be manufactured in a wide variety of sizes and shapes and from a wide variety of liquid-absorbing materials. An example of the formation of the absorbent structure is disclosed in Etz, U.S. Pat. No. 3,477,102, the disclosure of which is herein incorporated by reference.

The additive combination may be applied to the cover material in any manner that ensures sufficiently uniform coating. Many such methods are known to those of ordinary skill in the art. A representative, non-limiting list of useful methods includes spraying, extruding, slot coating, brushing, transfer coating, and the like. An individual sheet of the apertured film cover material may be applied to an absorbent structure, such as an absorbent sliver, in the manufacture of a tampon using a cut-and-place unit to cut the material from the slit roll and to place it on the absorbent structure. Another method of applying the cover is generally described in Friese, U.S. Pat. No. 4,816,100, the disclosure of which is herein incorporated by reference. While this describes the use of a nonwoven cover to a tampon, improvements necessary to achieve this are described in the commonly-assigned, copending application, U.S. Ser. No. 09/343,759, filed Jun. 30, 1999, entitled "Continuous Method of Providing Individual Sheets from a Continuous Web", the disclosure of which is herein incorporated by reference. This copending application discloses a method to achieve the total separation of a section of material comprises the following steps: severing a supply material in a plurality of discrete regions along a transverse axis, scoring the material residing between the severed regions along the same transverse axis, and then applying a force sufficient to fracture the scored regions, thereby separating the section of material from its supply. The cover and absorbent can then be rolled to form a covered tampon blank in which the individual sheet of the cover material substantially encloses the tampon blank.

Prior to applying the additive combination to the cover, the components of thereof can be combined in any manner useful to achieve the preferred combination. For example, the components can be combined in a vessel and stirred until a uniform mixture is achieved that can be recognized by a homogeneous appearance without phase separation. In some combination, the application of moderate amounts of heat will speed the mixing process. Generally, it will be beneficial to add the predominant component into the mixing vessel first. However, the components can also be added substantially simultaneously, or even in reverse order.

The covered tampon blank can then be formed into a tampon using a tampon press. One method is described in Wolff et al., U.S. Pat. No. 3,422,496, the disclosure of which is herein incorporated by reference. This method includes expulsion of a compressed tampon out of a tampon press by means of a ram. This expulsion is axial or along the direction of the press axis, and it is readily understood that expulsion forces can be quite high due to frictional forces between the compressed tampon and the jaw members that formed the compressed tampon. While it may be possible to reduce the frictional forces by withdrawing the jaw members slightly away from the press axis, the radial expulsion of the compressed tampon still provides a significantly high expulsion force.

Another method is described in Friese et al. U.S. Pat. Ser. No. 07/596,454, filed Oct. 12, 1990, and EP-B-0 422 660, the disclosures of which are herein incorporated by reference. The jaw members of this type of tampon press are modified in comparison to that those of Wolff et al. The jaw members of Friese et al. incorporate press cutters or fingers that project into the compressed tampon. Thus, this process can result in even higher expulsion forces than the process of Wolff et al.

The present invention will be further understood by reference to the following specific Examples which are illustrative of the composition, form and method of producing the present invention. It is to be understood that many variations of composition, form and method of producing this would be apparent to those skilled in the art. The following Examples, wherein parts and percentages are by weight unless otherwise indicated, are only illustrative.

EXAMPLES

Example 1

The effectiveness of coating materials for fluid transfer across the apertured polymeric film web was measured using the "Sinking Basket Test", described below.

Apertured polymeric films prepared by coextruding two polymeric blends through multiple extruders. The two melt streams entered a feed block that split the outside layer polymer blend into two streams, leaving the intermediate layer intact. The outer layers thus enclosed or "sandwiched" the intermediate layer to produce an A-B-A film with the proportions of polymer indicated in Table 1, below. The A-layers are evenly divided, so a 50:50 proportion of A:B would actually provide a 25:50:25 distribution when both A-layers are considered.

TABLE 1

| Film | A-layers (wt-%) | B-Layers (wt-%) |
| --- | --- | --- |
| Film 1 | 50 | 50 |
| Film 2 | 86 | 14 |
| Film 3 | 89 | 11 |

The A-layer composition is indicated in Table 2, below, in which LDPE is low density polyethylene, LLDPE is linear low density PE, HDPE is high density polyethylene, Metallocene is metallocene-catalyzed polyethylene, and $TiO_2$ concentrate is a pigment concentrate comprising about 50–70 wt-% $TiO_2$ dispersed in a polyolefin, such as polyethylene.

TABLE 2

| Film | LDPE (wt-%) | LLDPE (wt-%) | HDPE (wt-%) | Metallocene (wt-%) | TiO$_2$ Concentrate (wt-%) |
|---|---|---|---|---|---|
| Film 1 | 70 | | | 30 | |
| Film 2 | 49 | 30 | 15 | | 6 |
| Film 3 | 54 | 15 | 25 | | 6 |

The B-layer composition is indicated in Table 3, below, in which HDPE and LDPE are as above for the A-layer and PP is polypropylene:

TABLE 3

| Film | PP (wt-%) | LDPE (wt-%) | HDPE (wt-%) |
|---|---|---|---|
| Film 1 | | 30 | 70 |
| Film 2 | 100 | | |
| Film 3 | 100 | | |

Film 1 was provided by Isofilme, Sao Paulo, Brazil, and Films 2 and 3 were provided by Guial, Quinceux, France.

The A-B-A film was then apertured by applying jets of hot air and vacuum at about 330° C. while being supported by a cylindrical forming surface substantially as described in James et al., U.S. Pat. No. 5,916,462, and Zimmerli, U.S. Pat. No. 3,054,148. The differences between the disclosures therein and the process used herein would not be expected to change the results described hereinbelow. The resulting apertured film had a repeating pattern of substantially uniform, round apertures, an open area of about 23–25%, and an equivalent hydraulic diameter ("EHD"), as measured by the formula EHD=4*area/perimeter, of about 23–25 mils (0.58–0.64 mm).

Open area may be determined by using image analysis to measure the relative percentages of apertured and unapertured, or land, areas. Essentially image analysis converts an optical image from a light microscope into an electronic signal suitable for processing. An electronic beam scans the image, line-by-line. As each line is scanned, an output signal changes according to illumination. White areas produce a relatively high voltage and black areas a relatively low voltage. An image of the apertured formed film is produced and, in that image, the holes are white, while the solid areas of thermoplastic material are at various levels of gray. The more dense the solid area, the darker the gray area produced. Each line of the image that is measured is divided into sampling points or pixels. The following equipment can be used to carry out the analysis described above: a Quantimet Q520 Image Analyzer (with v. 5.02B software and Grey Store Option), sold by LEICA/Cambridge Instruments Ltd., in conjunction with an Olympus SZH Microscope with a transmitted light base, a plan 1.0× objective, and a 2.50× eyepiece. The image can be produced with a DAGE MTI CCD72 video camera.

A representative piece of each material to be analyzed is placed on the microscope stage and sharply imaged on the video screen at a microscope zoom setting of 10×. The open area is determined from field measurements of representative areas. The Quantimet program output reports mean value and standard deviation for each sample.

EHD was measured according to the procedure disclosed in Turi et al., U.S. Pat. No. 5,567,376. However, the image was acquired using a ScanJet 4c scanner from Hewlett-Packard, Palo Alto, Calif., USA, and analyzed using Image-Pro software from Media Cybernetics, Silver Springs, Md., USA. These changes do not significantly alter any results.

The apertured film was coated with the test materials by spray coating with two spray nozzles. The coating weight is determined by NMR according to the following procedure:

Test Equipment and Reagents:
Oxford QP+20 NMR analyzer
Test tubes 18 mm ID×180 mm, marked at 1.5 inches from bottom (Oxford #QP1 001)
Analytical balance (±0.2 mg accuracy)
Sample Preparation
Samples having a weight of approximately 2 g.
Test performance
1. Calibrate NMR with known amount of film coatings/weights (approximately 24 samples) and establish a calibration curve.
2. Weigh a film (approx. 2 g) with unknown amount of known coating, place the film into a test tube and pack with glass tube below the 1.5 inch mark, being careful to avoid excessive sample handling.
3. Place test tube into the NMR analyzer.
4. Enter the sample weight.
5. Report results as coating wt-% shown on the NMR analyzer display.

The Sinking Basket Test was performed on these apertured film samples as follows:

Sinking Basket Test Procedure

Test Equipment and Reagents:
Precision balance, accurate to 0.01 g
Stop watch
Beaker (diameter 10–13 cm, height 20 cm)
Water of about 20° C.
Dry cylindrical baskets consisting of copper wire with a diameter of 0.4 mm. These baskets have a height of 8.0 cm and a diameter of 5.0 cm. The mesh is 1.5 to 2.0 cm and the mass is 2.7+/−0.3 g.
Sample Preparation
At least 3 cover material samples of exactly 5.0+/−0.1 g are prepared.
Test Performance
The basket is weighed to the nearest centigram. 5 g of the cover material (pieces of 1.0–1.8 m in length; slit width ~50 mm) is placed loosely (randomly stuffing) in the basket. Then the basket is weighed to the nearest centigram. A beaker with a diameter of 10–13 cm is filled with water of about 20° C. to a height of 15–18 cm. The filled basket is held horizontally and dropped from a height of about 10 mm onto the water. The time which the basket takes to sink below the water surface is measured with a stop watch. The sinking time is calculated as the average of the results of the three or more tests. (Source: European Pharmocopoeia, Europäisches Arzneibuch, 3. Edition 1997, Deutscher Apotheker Verlag Stuttgart, page 1808). The materials and the basket sink time are reported in Table 4, below.

TABLE 4

| Cover | Coating | Add-on (%) | Sinking time (sec) | Std. Dev. (sec) |
|---|---|---|---|---|
| Film 1 | None (Control) | N/A | >>180 | |
| Film 2 | None (Control) | N/A | >>180 | |

TABLE 4-continued

| Cover | Coating | Add-on (%) | Sinking time (sec) | Std. Dev. (sec) |
|---|---|---|---|---|
| Film 3 | None (Control) | N/A | >>180 | |
| Film 1 | TWEEN 20 | 1.0 | 36.0 | / |
| Film 1 | SPAN 80 | 1.0 | 45.5 | / |
| Film 1 | PEG 400 | 1.0 | >>180 | |
| Film 1 | PEG 600 | 1.0 | >>180 | |
| Film 1 | SPAN 80 | 1.0 | 45.5 | / |
| Film 2 | SPAN 80 | 2.0 | 39.2 | 7.6 |
| Film 2 | 9% PEG 400/81% SPAN 80 | 1.1 | 20.8 | 4.5 |
| Film 2 | 23% PEG 400/77% SPAN 80 | 1.3 | 3.1 | 1.0 |
| Film 2 | 25% PEG 400/75% SPAN 80 | 1.0 | 2.4 | 0.3 |
| Film 2 | 33% PEG 400/67% SPAN 80 | 1.5 | 2.1 | 0.2 |
| Film 3 | 50% PEG 400/50% SPAN 80 | 1.0 | 1.9 | 0.1 |
| Film 3 | 75% PEG 400/25% SPAN 80 | 1.6 | 1.6 | 0.0 |
| Film 3 | 90% PEG 400/10% SPAN 80 | 1.7 | 2.5 | 0.5 |
| Film 3 | 25% Propylene Glycol/75% SPAN 80 | 1.6 | 10.9 | 0.8 |
| Film 3 | 50% Propylene Glycol/50% SPAN 80 | 1.6 | 5.2 | 0.4 |
| Film 3 | 75% Propylene Glycol/25% SPAN 80 | 1.4 | 8.8 | 0.7 |
| Film 3 | 50% SPAN 80/50% TWEEN 20 | 1.4 | 4.0 | 0.2 |

The trial illustrates that coatings formed of mixtures of a diol and a surfactant provide significantly improved sinking basket performance than coatings formed of the individual components alone. Such mixtures provide a sinking basket time of less than 25 seconds.

The specification and embodiments above are presented to aid in the complete and non-limiting understanding of the invention disclosed herein. Since many variations and embodiments of the invention can be made without departing from its spirit and scope, the invention resides in the claims hereinafter appended.

What is claimed is:

1. A polymeric film material useful as a body-side cover of an absorbent article, the film material comprising:
   a) an apertured polymeric film web; and
   b) an additive combination comprising:
      i) about 10 to about 90 wt-% of a diol; and
      ii) about 90 to about 10 wt-% of a surfactant;
   wherein the film material exhibits a sinking basket test time of less than about 25 seconds.

2. The material of claim 1 wherein the material comprises up to about 1 gsm of the additive combination.

3. The material of claim 2 wherein the material comprises about 0.05 to about 0.8 gsm of the additive combination.

4. The material of claim 3 wherein the material comprises about 0.2 to about 0.5 gsm of the additive combination.

5. The material of claim 1 wherein the additive combination comprises about 25 to about 75 wt-% of the diol and about 75 to about 25 wt-% of the surfactant.

6. The material of claim 5 wherein the additive combination comprises about 40 to about 60 wt-% of the diol and about 60 to about 40 wt-% of the surfactant.

7. The material of claim 1 wherein the diol is a polyglycol.

8. The material of claim 7 wherein the polyglycol is selected from the group consisting of polyethylene glycol, polypropylene glycol, polybutylene glycol, a block copolymer of butylene oxide and ethylene oxide, and combinations thereof.

9. The material of claim 8 wherein the additive combination is polyethylene glycol.

10. The material of claim 1 wherein the surfactant has an HLB value of less than about 17.

11. The material of claim 10 wherein the surfactant has an HLB value of less than about 8.

12. The material of claim 11 wherein the surfactant has an HLB value of less than about 5.

13. The material of claim 1 wherein the surfactant is selected from the group consisting of nonionic surfactants, anionic surfactants, cationic surfactants, and combinations thereof.

14. The material of claim 13 wherein the surfactant comprises a nonionic surfactant.

15. The material of claim 14 wherein the surfactant is selected from the group consisting of sorbitan fatty acid esters, polyoxyethylene alcohols, polyoxyethylene polyol fatty acid esters, polyoxyethylene fatty acid ethers, methyl glucose derivatives and combinations thereof.

16. A catamenial tampon comprising an absorbent structure substantially enclosed within a polymeric film material disposed on at least one body-facing of an absorbent article and a withdrawal string, the film material comprising:
   a) an apertured polymeric film web; and
   b) an additive combination comprising:
      i) about 10 to about 90 wt-% of a diol; and
      ii) about 90 to about 10 wt-% of a surfactant;
   wherein the film material provides a sinking basket test time of less than about 25 seconds.

17. The tampon of claim 16 wherein the material comprises up to about 1 gsm of the additive combination.

18. The tampon of claim 17 wherein the material comprises about 0.05 to about 0.8 gsm of the additive.

19. The tampon of claim 18 wherein the material comprises about 0.2 to about 0.5 gsm of the additive.

20. The tampon of claim 16 wherein the additive combination comprises about 25 to about 75 wt-% of the diol and about 75 to about 25 wt-% of the surfactant.

21. The tampon of claim 20 wherein the additive combination comprises about 40 to about 60 wt-% of the diol and about 60 to about 40 wt-% of the surfactant.

22. The tampon of claim 16 wherein the diol is a polyglycol.

23. The tampon of claim 22 wherein the polyglycol is selected from the group consisting of polyethylene glycol, polypropylene glycol, polybutylene glycol, a block copolymer of butylene oxide and ethylene oxide, and combinations thereof.

24. The tampon of claim 23 wherein the additive combination is polyethylene glycol.

25. The tampon of claim 16 wherein the surfactant has an HLB value of less than about 17.

26. The tampon of claim 25 wherein the surfactant has an HLB value of less than about 8.

27. The tampon of claim 26 wherein the surfactant has an HLB value of less than about 5.

28. The tampon of claim 16 wherein the surfactant is selected from the group consisting of nonionic surfactants, anionic surfactants, cationic surfactants, and combinations thereof.

29. The tampon of claim 28 wherein the surfactant comprises a nonionic surfactant.

30. The tampon of claim 29 wherein the surfactant is selected from the group consisting of sorbitan fatty acid esters, polyoxyethylene alcohols, polyoxyethylene polyol fatty acid esters, polyoxyethylene fatty acid ethers, methyl glucose derivatives and combinations thereof.

31. A process for the manufacture of a tampon comprising:
   a) applying up to about 1 gsm of an additive composition to a web of fluid-impervious plastic material formed into an apertured film material, the additive combination comprising:
 i) about 10 to about 90 wt-% of a diol; and
 ii) about 90 to about 10 wt-% of a surfactant;
wherein the film material provides a sinking basket test time of less than about 25 seconds;
 b) separating an individual sheet from the web;
 c) attaching the individual sheet to an absorbent sliver;
 d) forming the absorbent sliver into a tampon blank wherein the individual sheet substantially encloses the tampon blank;
 e) compressing the tampon blank in a press to form a substantially cylindrical, compressed tampon having a cover comprising the individual sheet; and
 f) applying an ejection force to the compressed tampon in an axial direction to eject the tampon from the press.

32. The process of claim 31 comprising coating the web of fluid-impervious plastic material with about 0.05 to about 0.8 gsm of the additive combination.

33. The process of claim 32 comprising coating the web of fluid-impervious plastic material with about 0.2 to about 0.5 gsm of the additive combination.

34. The process of claim 31 wherein the additive combination comprises about 25 to about 75 wt-% of the diol and about 75 to about 25 wt-% of the surfactant.

35. The process of claim 34 wherein the additive combination comprises about 40 to about 60 wt-% of the diol and about 60 to about 40 wt-% of the surfactant.

36. The process of claim 31 wherein the diol is a polyglycol.

37. The process of claim 36 wherein the polyglycol is selected from the group consisting of polyethylene glycol, polypropylene glycol, polybutylene glycol, a block copolymer of butylene oxide and ethylene oxide, and combinations thereof.

38. The process of claim 37 wherein the polyglycol is polyethylene glycol.

* * * * *